US008121698B2

(12) United States Patent
Fridman et al.

(10) Patent No.: US 8,121,698 B2
(45) Date of Patent: Feb. 21, 2012

(54) OUTER HAIR CELL STIMULATION MODEL FOR THE USE BY AN INTRA-COCHLEAR IMPLANT

(75) Inventors: Gene Y. Fridman, Santa Clarita, CA (US); Leonid M. Litvak, Los Angeles, CA (US)

(73) Assignee: Advanced Bionics, LLC, Valencia, CA (US)

( * ) Notice: Subject to any disclaimer, the term of this patent is extended or adjusted under 35 U.S.C. 154(b) by 88 days.

(21) Appl. No.: 12/728,722

(22) Filed: Mar. 22, 2010

(65) Prior Publication Data
US 2010/0179616 A1 Jul. 15, 2010

Related U.S. Application Data

(60) Continuation of application No. 11/765,395, filed on Jun. 19, 2007, now abandoned, which is a division of application No. 11/003,155, filed on Dec. 3, 2004, now Pat. No. 7,242,985.

(51) Int. Cl.
*A61N 1/08* (2006.01)
(52) U.S. Cl. .............. 607/55; 607/56; 607/57; 607/136; 607/137
(58) Field of Classification Search ............... 607/55, 607/56, 57, 136, 137
See application file for complete search history.

(56) References Cited

U.S. PATENT DOCUMENTS

| 4,532,930 | A | 8/1985 | Crosby et al. |
| 4,612,934 | A | 9/1986 | Borkan |
| 4,793,353 | A | 12/1988 | Borkan |
| 4,819,647 | A | 4/1989 | Byers et al. |
| 4,905,285 | A | 2/1990 | Allen et al. |
| 5,749,912 | A | 5/1998 | Zhang et al. |
| 5,991,663 | A | 11/1999 | Irlicht et al. |
| 6,064,913 | A | 5/2000 | Irlicht et al. |
| 6,078,838 | A | 6/2000 | Rubinstein |

(Continued)

FOREIGN PATENT DOCUMENTS

WO 2004/043537 5/2004

(Continued)

OTHER PUBLICATIONS

U.S. Appl. No. 60/950,324, Fridman et al., filed Jul. 17, 2007.

(Continued)

*Primary Examiner* — Carl H Layno
*Assistant Examiner* — Natasha Patel
(74) *Attorney, Agent, or Firm* — Wong, Cabello, Lutsch, Rutherford & Brucculeri LLP

(57) ABSTRACT

Contrast between various frequency components of sound is enhanced through a lateral suppression strategy to provide increased speech perception in the electrically stimulated cochlea. A received audio signal is divided into a plurality of input signals, wherein each input signal is associated with a frequency band. A plurality of envelope signals are generated by determining the envelope of each of a plurality of the input signals. At least one of the envelope signals is scaled in accordance with a scaling factor to generate at least one scaled envelope signal. An output signal is generated by combining at least one envelope signal with at least one scaled envelope signal, and the cochlea is stimulated based on the generated output signal. The lateral suppression strategy can be applied to one or more frequency bands using scaled amplitude signals associated with one or more neighboring frequency bands.

9 Claims, 7 Drawing Sheets

U.S. PATENT DOCUMENTS

| | | | |
|---|---|---|---|
| 6,129,753 A | 10/2000 | Kuzma | |
| 6,154,678 A | 11/2000 | Lauro | |
| 6,198,971 B1 | 3/2001 | Leysieffer | |
| 6,216,045 B1 | 4/2001 | Black et al. | |
| 6,219,580 B1 | 4/2001 | Faltys et al. | |
| 6,289,247 B1 * | 9/2001 | Faltys et al. | 607/57 |
| 6,308,101 B1 | 10/2001 | Faltys et al. | |
| 6,600,955 B1 | 7/2003 | Zierhofer | |
| 6,700,982 B1 | 3/2004 | Geurts et al. | |
| 6,728,578 B1 | 4/2004 | Voelkel | |
| 6,745,155 B1 | 6/2004 | Andringa et al. | |
| 6,775,389 B2 | 8/2004 | Harrison et al. | |
| 6,778,858 B1 | 8/2004 | Peeters | |
| 6,826,430 B2 | 11/2004 | Faltys et al. | |
| 6,915,166 B1 | 7/2005 | Stecker et al. | |
| 7,003,876 B2 | 2/2006 | Crawford et al. | |
| 7,083,332 B2 | 8/2006 | Mukouda | |
| 7,162,415 B2 | 1/2007 | Holzrichter et al. | |
| 7,171,272 B2 | 1/2007 | Blamey et al. | |
| 7,225,027 B2 | 5/2007 | Zeng et al. | |
| 7,277,760 B1 | 10/2007 | Litvak et al. | |
| 7,292,891 B2 | 11/2007 | Hartley et al. | |
| 7,292,892 B2 | 11/2007 | Litvak et al. | |
| 7,308,303 B2 | 12/2007 | Whitehurst et al. | |
| 7,310,558 B2 | 12/2007 | Van Hoesel | |
| 7,317,945 B2 | 1/2008 | Litvak et al. | |
| 7,347,746 B1 | 3/2008 | He | |
| 7,349,741 B2 | 3/2008 | Maltan et al. | |
| 7,376,466 B2 | 5/2008 | He et al. | |
| 7,426,445 B1 | 9/2008 | Fister | |
| 7,444,180 B2 | 10/2008 | Kuzma et al. | |
| 7,445,528 B1 | 11/2008 | Kuzma | |
| 7,450,994 B1 | 11/2008 | Mishra et al. | |
| 7,522,961 B2 | 4/2009 | Fridman et al. | |
| 7,599,500 B1 | 10/2009 | Segel et al. | |
| 7,627,383 B2 | 12/2009 | Haller et al. | |
| 7,660,631 B2 | 2/2010 | Whitehurst et al. | |
| 2003/0114905 A1 | 6/2003 | Kuzma | |
| 2004/0015204 A1 | 1/2004 | Whitehurst et al. | |
| 2004/0015205 A1 | 1/2004 | Whitehurst et al. | |
| 2004/0082980 A1 | 4/2004 | Mouine et al. | |
| 2004/0082985 A1 | 4/2004 | Faltys et al. | |
| 2004/0136556 A1 | 7/2004 | Litvak et al. | |
| 2004/0230254 A1 | 11/2004 | Harrison et al. | |
| 2005/0137651 A1 | 6/2005 | Litvak et al. | |
| 2005/0240229 A1 | 10/2005 | Whitehurst et al. | |
| 2005/0267555 A1 | 12/2005 | Marnfeldt et al. | |
| 2006/0100672 A1 | 5/2006 | Litvak | |
| 2006/0106446 A1 | 5/2006 | Fridman et al. | |
| 2006/0161204 A1 | 7/2006 | Colvin et al. | |
| 2006/0184204 A1 | 8/2006 | He | |
| 2006/0195143 A1 | 8/2006 | McClure et al. |
| 2006/0229688 A1 | 10/2006 | McClure et al. | |
| 2007/0021800 A1 | 1/2007 | Whitehurst et al. | |
| 2007/0049988 A1 | 3/2007 | Carbunaru et al. | |
| 2007/0055308 A1 | 3/2007 | Haller et al. | |
| 2007/0066997 A1 | 3/2007 | He et al. | |
| 2007/0100395 A1 | 5/2007 | Ibrahim | |
| 2007/0112403 A1 | 5/2007 | Moffitt et al. | |
| 2007/0112404 A1 | 5/2007 | Mann et al. | |
| 2007/0123938 A1 | 5/2007 | Haller et al. | |
| 2007/0219595 A1 | 9/2007 | He | |
| 2007/0239227 A1 | 10/2007 | Fridman | |
| 2007/0260292 A1 | 11/2007 | Faltys et al. | |
| 2007/0293785 A1 | 12/2007 | Litvak | |
| 2008/0065183 A1 | 3/2008 | Whitehurst et al. | |
| 2008/0085023 A1 | 4/2008 | Kulkarni et al. | |
| 2008/0132961 A1 | 6/2008 | Jaax et al. | |

FOREIGN PATENT DOCUMENTS

| | | |
|---|---|---|
| WO | 2006/053101 | 5/2006 |
| WO | 2007/030496 | 3/2007 |
| WO | 2007/059343 | 5/2007 |
| WO | 2007/130782 | 11/2007 |

OTHER PUBLICATIONS

U.S. Appl. No. 60/975,111, Kulkarni, filed Sep. 25, 2007.
U.S. Appl. No. 11/089,171, Hahn, filed Mar. 24, 2005.
U.S. Appl. No. 11/122,648, Griffith, filed May 5, 2005.
U.S. Appl. No. 11/178,054, Faltys, filed Jul. 8, 2005.
U.S. Appl. No. 11/226,777, Faltys, filed Sep. 13, 2005.
U.S. Appl. No. 11/261,432, Mann, filed Oct. 28, 2005.
U.S. Appl. No. 11/262,055, Fridman, filed Oct. 28, 2005.
U.S. Appl. No. 11/386,198, Saoji, filed Mar. 21, 2006.
U.S. Appl. No. 11/387,206, Harrison, filed Mar. 23, 2006.
U.S. Appl. No. 11/234,933, Faltys, filed Sep. 25, 2006.
U.S. Appl. No. 11/765,395, Fridman, filed Jun. 19, 2007.
Carney, L.H., "A model for the responses of low-frequency auditory-nerve fibers in cat", J. Acoust Soc. Am. 93(1):401-417 (1993).
Deutsch et al., "Understanding the Nervous system, An Engineering Perspective", IEEE Press, Chap. 9, pp. 181-225 (1993).
Geurts, L. and J. Wouters, "Enhancing the speech envelope of continuous interleaved sampling processors for cochlear implants", J. Acoust Soc. Am. 105(4):2476-84 (1999).
Moore, Brian C.J., "An Introduction to the Psychology of Hearing", 4$^{th}$ Edition, Academic Press, pp. 9-12 (1997).
Srulovicz et al., "A Central Spectrum Model: A Synthesis of Auditory-Nerve Timing and Place Cues in Monaural Communication of Frequency Spectrum", J. Acoust. Soc. Am., vol. 73, pp. 1266-1276 (1983).

* cited by examiner

SIMULTANEOUS ANALOGS STIMULATION BANDPASS FILTERS - EXTENDED FREQUENCY BOUNDARIES (Hz) — 410

| NUMBER OF CHANNELS | FILTER 1 | FILTER 2 | FILTER 3 | FILTER 4 | FILTER 5 | FILTER 6 | FILTER 7 | FILTER 8 |
|---|---|---|---|---|---|---|---|---|
| 8 CHANNELS | 250-500 | 500-875 | 875-1150 | 1150-1450 | 1450-2000 | 2000-2600 | 2600-3800 | 3800-6800 |
| 7 CHANNELS | 250-500 | 500-875 | 875-1150 | 1150-1450 | 1450-2000 | 2000-2600 | 2600-6800 | |
| 6 CHANNELS | 250-500 | 500-875 | 875-1150 | 1150-1750 | 1750-2600 | 2600-6800 | | |
| 5 CHANNELS | 250-500 | 500-875 | 875-1450 | 1450-2600 | 2600-6800 | | | |
| 4 CHANNELS | 250-875 | 875-1450 | 1450-2600 | 2600-6800 | | | | |
| 3 CHANNELS | 250-875 | 875-2600 | 2600-6800 | | | | | |
| 2 CHANNELS | 350-700 | 2200-4400 | | | | | | |
| 1 CHANNEL | 250-6800 | | | | | | | |

CIS BANDPASS FILTERS - EXTENDED FREQUENCY BOUNDARIES (Hz) — 420

| NUMBER OF CHANNELS | FILTER 1 | FILTER 2 | FILTER 3 | FILTER 4 | FILTER 5 | FILTER 6 | FILTER 7 | FILTER 8 |
|---|---|---|---|---|---|---|---|---|
| 8 CHANNELS | 250-500 | 500-730 | 730-1015 | 1015-1450 | 1450-2000 | 2000-2600 | 2600-3800 | 3800-6800 |
| 7 CHANNELS | 250-500 | 500-730 | 730-1015 | 1015-1450 | 1450-2000 | 2000-2600 | 2600-6800 | |
| 6 CHANNELS | 250-580 | 580-875 | 875-1150 | 1150-1750 | 1750-2600 | 2600-3800 | | |
| 5 CHANNELS | 250-580 | 580-1015 | 1015-1750 | 1750-3300 | 2000-3300 | 3300-6800 | | |
| 4 CHANNELS | 250-730 | 730-1450 | 1450-2600 | 2600-6800 | | | | |
| 3 CHANNELS | 250-875 | 875-2000 | 2000-6800 | | | | | |
| 2 CHANNELS | 350-700 | 2200-4400 | | | | | | |
| 1 CHANNEL | 250-6800 | | | | | | | |

FIG. 4

OUTER HAIR CELL STIMULATION MODEL FOR THE USE BY AN INTRA-COCHLEAR IMPLANT

CROSS-REFERENCE TO RELATED APPLICATIONS

This application is a continuation of U.S. patent application Ser. No. 11/765,395, filed Jun. 19, 2007, which was in turn a divisional of U.S. patent application Ser. No. 11/003,155, filed Dec. 3, 2004 (now U.S. Pat. No. 7,242,985). Priority is claimed to both of these applications and both and incorporated herein by reference in their entireties.

TECHNICAL FIELD

The present disclosure relates to implantable neurostimulator devices and systems, for example, cochlear stimulation systems, and to sound processing strategies employed in conjunction with such systems.

BACKGROUND

Prior to the past several decades, scientists generally believed that it was impossible to restore hearing to the profoundly deaf. However, scientists have had increasing success in restoring normal hearing to the deaf through electrical stimulation of the auditory nerve. The initial attempts to restore hearing were not very successful, as patients were unable to understand speech. However, as scientists developed different techniques for delivering electrical stimuli to the auditory nerve, the auditory sensations elicited by electrical stimulation gradually came closer to sounding more like normal speech. The electrical stimulation is implemented through a prosthetic device, known as a cochlear implant, which is implanted in the inner ear to restore partial hearing to profoundly deaf patients.

Such cochlear implants generally employ an electrode array that is inserted into the cochlear duct. One or more electrodes of the array selectively stimulate different auditory nerves at different places in the cochlea based on the pitch of a received sound signal. Within the cochlea, there are two main cues that convey "pitch" (frequency) information to the patient. There are (1) the place or location of stimulation along the length of a cochlear duct and (2) the temporal structure of the stimulating waveform. In the cochlea, sound frequencies are mapped to a "place" in the cochlea, generally from low to high sound frequencies mapped from the apical to basilar direction. The electrode array is fitted to the patient to arrive at a mapping scheme such that electrodes near the base of the cochlea are stimulated with high frequency signals, while electrodes near the apex are stimulated with low frequency signals.

Accordingly, the present inventors recognized the need to account for the interaction between frequency bands and enhance the contrast between neighboring signals.

FIG. 1 presents a cochlear stimulation system 10 that includes a sound processor portion 12 and a cochlear stimulation portion 20. The sound processor portion 12 includes a microphone 14 and a sound processor 18. The microphone 14 can be connected directly to the sound processor 18. Alternatively, the microphone 14 can be coupled to the sound processor 18 through an appropriate communication link 16. The cochlear stimulation portion 20 includes an implantable cochlear stimulator 22 and an electrode array 24. The electrode array 24 is adapted to be inserted within the cochlea of a patient. The electrode array 24 includes a plurality of electrodes (not shown) that are distributed along the length of the array and are selectively connected to the implantable cochlear stimulator 22.

The electrode array 24 may be substantially as shown and described in U.S. Pat. Nos. 4,819,647 or 6,129,753, both patents incorporated herein by reference. Electronic circuitry within the implantable cochlear stimulator 22 allows a specified stimulation current to be applied to selected pairs or groups of the electrodes (not shown) included within the electrode array 24 in accordance with a specified stimulation pattern defined by the sound processor 18.

The sound processor 18 and the implantable cochlear stimulator 22 are electronically coupled through a suitable communication link 26. In an implementation, the microphone 14 and the sound processor 18 comprise an external portion of the cochlear stimulation system 10, and the implantable cochlear stimulator 22 and the electrode array 24 comprise an internal, or implanted, portion of the cochlear stimulation system 10. Thus, the communication link 26 is a transcutaneous (through the skin) link that allows power and control signals to be sent from the sound processor 18 to the implantable cochlear stimulator 22.

In another implementation, the implantable cochlear stimulator 22 can send information, such as data and status signals, to the sound processor 18 over the communication link 26. In order to facilitate bidirectional communication between the sound processor 18 and the implantable cochlear stimulator 22, the communication link 26 can include more than one channel. Additionally, interference can be reduced by transmitting information on a first channel using an amplitude-modulated carrier and transmitting information on a second channel using a frequency-modulated carrier.

In an implementation in which the implantable cochlear stimulator 22 and the electrode array 24 are implanted within the patient, and the microphone 14 and the sound processor 18 are carried externally (not implanted) by the patient, the communication link 26 can be realized though use of an antenna coil in the implantable cochlear stimulator 22 and an external antenna coil coupled to the sound processor 18. The external antenna coil can be positioned so that it is aligned with the implantable cochlear stimulator 22, allowing the coils to be inductively coupled to each other and thereby permitting power and information, e.g., a stimulation signal, to be transmitted from the sound processor 18 to the implantable cochlear stimulator 22. In another implementation, the sound processor 18 and the implantable cochlear stimulator 22 can both be implanted within the patient, and the communication link 26 can be a direct-wired connection or other suitable link as shown in U.S. Pat. No. 6,308,101, incorporated herein by reference.

In the cochlear stimulation system 10, the microphone 14 senses acoustic signals and converts the sensed acoustic signals to corresponding electrical signals. The electrical signals are sent to the sound processor 18 over an appropriate communication link 16, such as a circuit or bus. The sound processor 18 processes the electrical signals in accordance with a sound processing strategy and generates control signals used to control the implantable cochlear stimulator 22. Such control signals can specify or define the polarity, magnitude, location (which electrode pair or group is intended to receive the stimulation current), and timing (when the stimulation current is to be applied to the intended electrode pair or group) of the stimulation signal, such as a stimulation current, that is generated by the implantable cochlear stimulator 22.

It is common in the cochlear stimulator art to condition the magnitude and polarity of the stimulation current applied to the implanted electrodes of the electrode array 24 in accordance with a specified sound processing strategy. A sound processing strategy involves defining a pattern of stimulation waveforms that are applied as controlled electrical currents to the electrodes of an electrode array 24 implanted in a patient. Stimulation strategies can be implemented by modulating the amplitude of the stimulation signal or by modulating the frequency of the stimulation signal.

SUMMARY

The methods and apparatus described here implement techniques for clarifying sound as perceived through a cochlear implant. More specifically, the methods and apparatus described here implement techniques for using the outer hair cell model to enhance contrasts between stimulation signals as perceived through a cochlear implant.

In general, in one aspect, the techniques can be implemented to include dividing an audio signal into a plurality of input signals, wherein each input signal is associated with a frequency band; generating a plurality of envelope signals, including at least a first and a second envelope signal, by determining an envelope of each of at least two input signals, each input signal being associated with a corresponding frequency band; scaling at least one of the envelope signals in accordance with a scaling factor to generate at least one scaled envelope signal; and combining at least one envelope signal with at least one scaled envelope signal to generate an output signal.

The techniques also can be implemented to include multiplying the first envelope signal by a first weighting factor and multiplying the second envelope signal by a second weighting factor. The techniques can further be implemented to include determining a separation between a first frequency band and a second frequency band, and selecting a scaling factor based on the separation. Additionally, the techniques can be implemented to include scaling a plurality of envelope signals associated with frequency bands that neighbor a first frequency band to generate a plurality of scaled envelope signals, and combining the envelope signal associated with the first frequency band with the plurality of scaled envelope signals to generate an output signal associated with the first frequency band.

The techniques also can be implemented to include rectifying an input signal prior to determining the envelope of the input signal. Further, the techniques can be implemented to include full-wave rectifying the input signal. Additionally, the techniques can be implemented to include setting an average amplitude associated with an input signal to zero at the beginning of a frame and determining the average amplitude associated with the input signal for the frame. The techniques also can be implemented such that the generated output signal comprises an acoustic signal. Further, the techniques can be implemented to include mapping the generated output signal to an electrical signal and applying the electrical signal to one or more electrode pairs of a cochlear implant. Additionally, the techniques can be implemented such that the generated output signal is associated with a first frequency band.

The techniques also can be implemented such that combining further comprises generating an output signal in accordance with a frequency modulated stimulation strategy, such as that described in U.S. patent application Ser. No. 10/917,789, incorporated herein by reference. Further, the techniques can be implemented to include subtracting the at least one scaled envelope signal from the at least one envelope signal. Additionally, the techniques can be implemented such that scaling at least one of the envelope signals reduces the magnitude of the envelope signal. The techniques also can be implemented such that each of the plurality of envelope signals represents an average amplitude of a corresponding input signal. Further, the techniques can be implemented such that scaling in accordance with a scaling factor comprises using a scaling factor which ranges from 0 to 1.

In general, in another aspect, the techniques can be implemented to include a plurality of filters configured to divide an audio signal into a plurality of input signals, wherein each input signal is associated with a frequency band; a plurality of envelope detectors configured to generate a plurality of envelope signals, including at least a first and a second envelope signal, by determining an envelope of each of at least two input signals, each input signal being associated with a corresponding frequency band; and circuitry configured to scale at least one of the envelope signals in accordance with a scaling factor to generate at least one scaled envelope signal and to combine at least one envelope signal with at least one scaled envelope signal to generate an output signal.

The techniques also can be implemented to include circuitry configured to multiply the first envelope signal by a first weighting factor and multiply the second envelope signal by a second weighting factor. The techniques also can be implemented to include circuitry configured to determine a separation between a first frequency band and a second frequency band, and select a scaling factor based on the separation. Additionally, the techniques can be implemented to include circuitry configured to scale a plurality of envelope signals associated with frequency bands that neighbor a first frequency band to generate a plurality of scaled envelope signals and combine the envelope signal associated with the first frequency band with the plurality of scaled envelope signals to generate an output signal associated with the first frequency band.

The techniques also can be implemented to include a rectifier configured to rectify an input signal prior to the envelope detector determining the envelope of the input signal. Further, the techniques can be implemented such that the rectifier comprises a full-wave rectifier. Additionally, the techniques can be implemented such that the envelope detector is configured to set an average amplitude associated with an input signal to zero at the beginning of a frame and determine the average amplitude associated with the input signal for the frame. The techniques can also be implemented such that the generated output signal comprises an acoustic signal.

The techniques also can be implemented to include circuitry configured to map the generated output signal to an electrical signal and apply the electrical signal to one or more electrode pairs of a cochlear implant. Further, the techniques can be implemented such that the generated output signal is associated with a first frequency band. Additionally, the techniques can be implemented to include circuitry configured to generate the output signal in accordance with a frequency modulated stimulation strategy.

The techniques also can be implemented to include circuitry configured to subtract the at least one scaled envelope signal from the at least one envelope signal. Further, the techniques can be implemented such that scaling at least one of the envelope signals reduces the magnitude of the envelope signal. Additionally, the techniques can be implemented such that each of the plurality of envelope detectors is configured to generate an envelope signal representing an average amplitude of a corresponding input signal. Further, the techniques can be implemented such that the circuitry comprises one or more of a programmable logic device, a field programmable gate array, an application-specific integrated circuit, and a general purpose processor executing programmed instructions. The techniques can also be implemented such that the scaling factor ranges from 0 to 1.

In general, in another aspect, the techniques can be implemented to include dividing an audio signal into at least a first input signal and a second input signal, wherein each input signal is associated with a frequency band; determining an effect of the second input signal on the first input signal; and subtracting the effect of the second input signal from the first input signal to generate an output signal.

The techniques described in this specification can be implemented to realize one or more of the following advantages. For example, the techniques can be implemented to enhance the contrast between neighboring stimulation signals of a sound processing strategy and thus improve sound clarity and speech recognition, especially under difficult listening conditions. The techniques also can be implemented to decrease the power consumption of a cochlear implant system implementing a sound processing strategy. Further, the techniques can be implemented to reduce interaction between neighboring electrodes and the resulting influence on corresponding neurons by decreasing the stimulation level on one or more electrodes as a result of the stimulation level present on one or more neighboring electrodes.

These general and specific aspects can be implemented using an apparatus, a method, a system, or any combination of an apparatus, methods, and systems. The details of one or more implementations are set forth in the accompanying drawings and the description below. Further features, aspects, and advantages will become apparent from the description, the drawings, and the claims.

BRIEF DESCRIPTION OF THE DRAWINGS

FIG. 4 presents exemplary frequency maps that can be used in conjunction with a sound processing strategy.

Like reference symbols indicate like elements throughout the specification and drawings.

DETAILED DESCRIPTION

Figure 1:
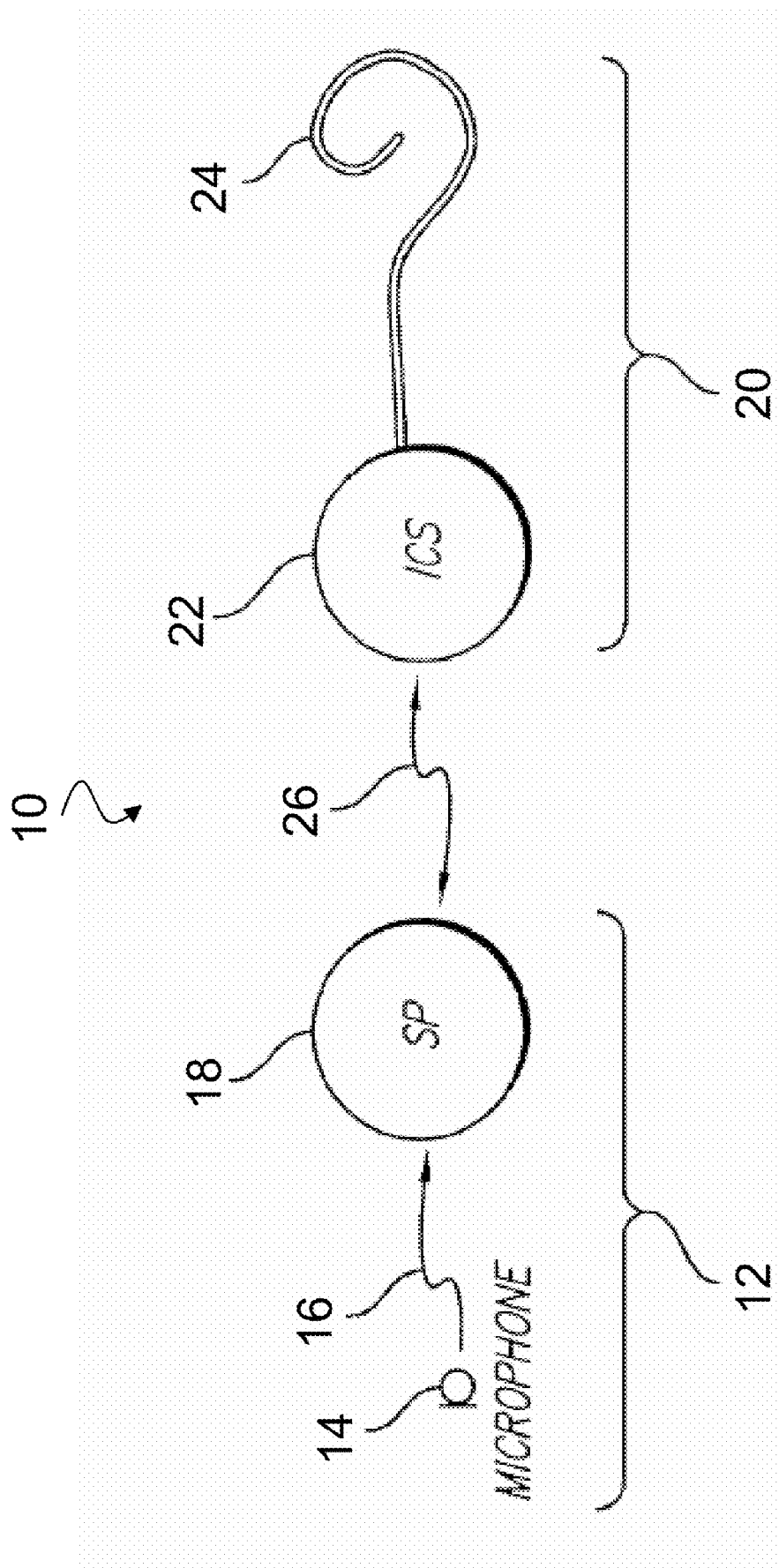
FIG. 1 is a block diagram of a cochlear stimulation system.
Figure 2:
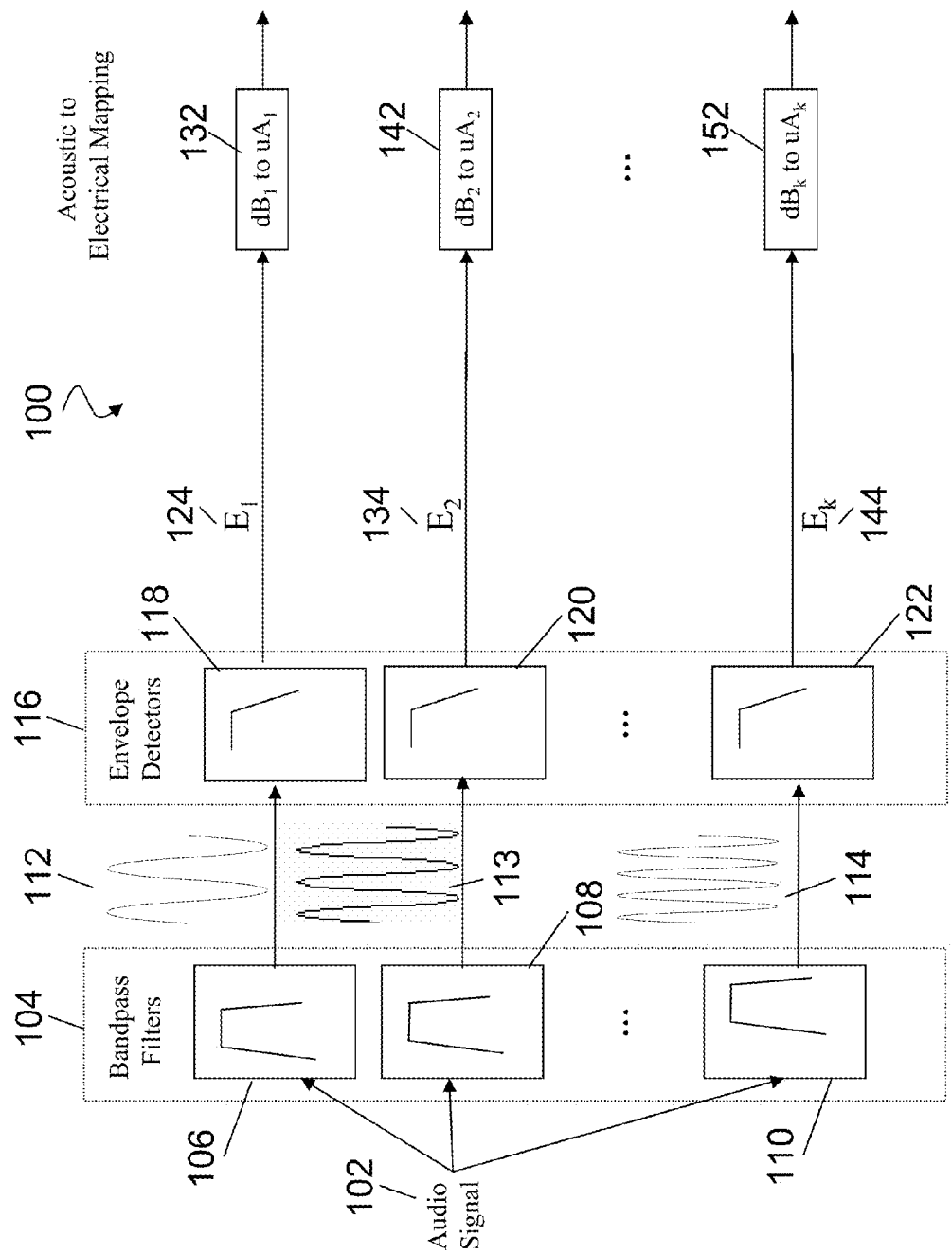
FIGS. 2-3 show a functional block diagram of a sound processing system.

FIG. 2 presents a functional block diagram of a conventional system arranged to implement a sound processing strategy. In the conventional sound processing system 100, an audio signal 102 is provided as an input to a bank of bandpass filters 104, which separates the audio signal 102 into individual frequency bands or channels. For example, if the audio signal 102 is provided to a bank of K bandpass filters, then the audio signal 102 is separated into K individual frequency bands. In another implementation, different types and combinations of filters can be employed to separate the audio signal 102 into individual frequency bands, such as notch filters, high-pass filters, and low-pass filters.

As the audio signal 102 is provided to the bank of bandpass filters 104, individual bandpass filters output filtered signals. For example, the bank of bandpass filters 104 includes a bandpass filter 106 corresponding to a first frequency band, a bandpass filter 108 corresponding to a second frequency band, and a bandpass filter 110 corresponding to a $k_{th}$ frequency band. As the audio signal 102 is provided to the bank of bandpass filters 104, the bandpass filter 106 corresponding to the first frequency band outputs a filtered signal 112 associated with the first frequency band, the bandpass filter 108 corresponding to the second frequency band outputs a filtered signal 113 associated with the second frequency band, and the bandpass filter 110 corresponding to the $k_{th}$ frequency band outputs a filtered signal 114 associated with the $k_{th}$ frequency band. Thus, each filtered signal is associated with a frequency band that represents a subset of the audio signal 102.

The bank of envelope detectors 116 includes an envelope detector 118 corresponding to the first frequency band, an envelope detector 120 corresponding to the second frequency band, and an envelope detector 122 corresponding to the $k_{th}$ frequency band. The envelope detectors of the bank of envelope detectors 116 receive as input filtered signals output from the corresponding bandpass filters in the bank of bandpass filters 104. For example, the envelope detector 118 corresponding to the first frequency band receives as input the filtered signal 112 associated with the first frequency band from the bandpass filter 106 corresponding to the first frequency band.

Each envelope detector of the bank of envelope detectors 116 is configured to determine an envelope associated with a received filtered signal and to output a representative envelope signal. For example, the filtered signal 112 associated with the first frequency band is input to the envelope detector 118 corresponding to the first frequency band, which determines the envelope of the filtered signal 112 and outputs an envelope signal $E_1$ 124 associated with the first frequency band. Similarly, the filtered signal 113 associated with the second frequency band is input to the envelope detector 120 corresponding to the second frequency band, which determines the envelope of the filtered signal 113 and outputs an envelope signal $E_2$ 134 associated with the second frequency band. Additionally, the filtered signal 114 associated with the $k_{th}$ frequency band is input to the envelope detector 122 corresponding to the $k_{th}$ frequency band, which determines the envelope of the filtered signal 114 and outputs an envelope signal $E_k$ 144 associated with the $k_{th}$ frequency band.

The envelope signals output from the bank of envelope detectors 116 are converted to electrical signals using acoustic-to-electrical mappings. Each of the resulting electrical signals is then applied to electrodes of a cochlear implant to provide a stimulation signal. For example, the envelope signal $E_1$ 124 output from the envelope detector 118 corresponding to the first frequency band is converted from an acoustic signal to an electrical signal using the acoustic-to-electrical mapping 132 associated with the first frequency band. Similarly, the envelope signals $E_2$ 134 and $E_k$ 144 are converted to electrical signals using the acoustic-to-electrical mappings 142 and 152 associated with the second frequency band and the $k_{th}$ frequency band respectively.

As described above, sound processing strategies do not account for the interaction of signals associated with neighboring frequency bands. A signal corresponding to a particular frequency band is either provided to an electrode array as a stimulation signal at full strength or the signal is completely suppressed. For example, the N of M algorithm simply determines the amplitude of the signals on each of M frequency bands and selects the N signals with the highest amplitudes to provide as stimulation signals. The remaining M-N signals are completely suppressed.

Further, sound processing strategies used to generate stimulation signals often incorporate the assumption that each frequency band, or channel, is represented independently in the cochlea. This assumption can result in poor sound quality and decreased comprehension of speech under difficult listening conditions, such as listening in a noisy environment. One factor believed to contribute to the poor performance is the interaction that occurs between frequency bands in cochlear implant subjects. Such frequency band interaction can smear or distort peaks in the stimulation signal that are essential to the identification of sounds.

Figure 3:
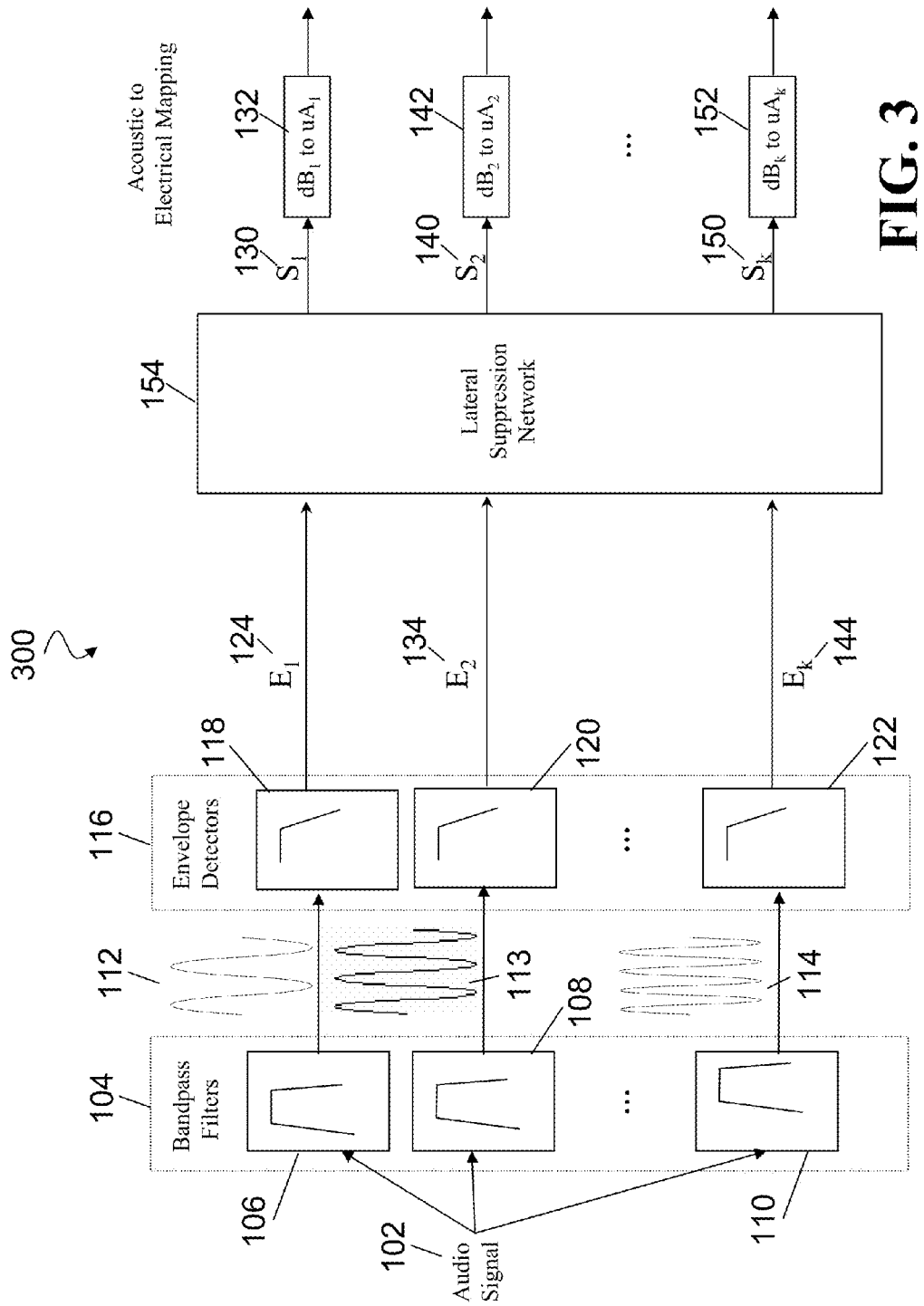

Similar to FIG. 2, FIG. 3 presents a functional block diagram of a system arranged to implement a sound processing strategy. Such sound processing strategy can be implemented using any combination of circuitry and programmed instructions, including one or more of a programmable logic device, a field-programmable gate array, an application-specific integrated circuit, and a general purpose processor executing programmed instructions.

In the system 300, an audio signal 102 is also provided to a bank of bandpass filters 104, which separates the audio signal 102 into a plurality of frequency bands or channels. The bank of bandpass filters 104 can be configured to separate the audio signal 102 into frequency bands that correspond to frequencies defined in a frequency map associated with a specific sound processing strategy. FIG. 4 presents an example of a frequency map associated with the Simultaneous Analog Stimulation (SAS) strategy 410 and a frequency map associated with the Continuous Interleaved Sampler (CIS) strategy 420. Other sound processing strategies, such as the Frequency Modulated Stimulation (FMS) strategy, can be implemented using either of the frequency maps presented in FIG. 4, or by using alternative frequency maps.

In another implementation, the audio signal 102 can undergo other processing before being provided as input to the bank of bandpass filters 104. For example, the audio signal 102 may originate as acoustic information sensed by a microphone, which is then converted into an electrical signal representing an audio signal. The electrical signal can further be converted to a digital signal in an analog-to-digital converter, and then subjected to automatic gain control (AGC) processing using an AGC algorithm. The AGC algorithm serves to compress the dynamic range of the audio signals to provide a more consistent level of stimulus to the electrodes and to equalize the level between sound sources that are removed from the listener by differing distances.

As discussed above, the bank of envelope detectors 116 includes an envelope detector 118 corresponding to the first frequency band, an envelope detector 120 corresponding to the second frequency band, and an envelope detector 122 corresponding to the $k_{th}$ frequency band. The envelope detectors of the bank of envelope detectors 116 receive as input filtered signals output from the corresponding bandpass filters in the bank of bandpass filters. For example, the envelope detector 118 corresponding to the first frequency band receives as input the filtered signal 112 associated with the first frequency band from the bandpass filter 106 corresponding to the first frequency band. Each of the envelope detectors of the bank of envelope detectors 116 can include a rectifier, such as a half-wave rectifier or a full-wave rectifier, that rectifies the filtered signal output from the corresponding bandpass filter of the bank of bandpass filters 104 before the envelope of the filtered signal is determined.

In an implementation, the envelope detectors included in the bank of envelope detectors 116 can comprise integrators that determine an average amplitude of a signal for a given interval. For example, upon receiving the filtered signal 112 associated with the first frequency band, the envelope detector 118 corresponding to the first frequency band determines an envelope of the filtered signal 112 for an interval, such as a frame. At the end of the interval, the envelope detector 118 corresponding to the first frequency band outputs the envelope signal $E_1$ 124, which represents the average amplitude of the filtered signal 112 associated with the first frequency band for that interval. Each envelope detector of the bank of envelope detectors 116 also can be configured to set the average amplitude value of a received filtered signal to an initial state prior to or at the start of a new interval.

The bank of envelope detectors outputs envelope signals representing acoustic signal values. However, unlike the prior art describe with reference to FIG. 2, the envelope signals are not converted to electrical signals using an acoustic-to-electrical mapping. Instead, the envelope signals are transferred to a lateral suppression network 154, which accounts for the interaction between envelope signals of neighboring frequency bands through the use of a lateral suppression model, such as the outer hair cell model, and outputs suppressed signals. A lateral suppression model, such as the outer hair cell model, can be used in conjunction with either a frequency modulated sound processing strategy, such as FMS, or an amplitude modulated stimulation strategy, such as CIS. The lateral suppression network 154 is discussed in greater detail with reference to FIG. 5.

Lateral suppression is the term used to describe the psychophysical effect by which the loudness perceived from one tone is diminished to some extent by the presence of a neighboring tone. The suppressive effect is particularly evident when a loud tone closely neighbors a quieter tone. Thus, lateral suppression operates to enhance the contrast between tones. However, the lateral suppression algorithm must be implemented such that it does not generate abnormal results. If a flat spectrum is input to the lateral suppression network 154, a flat spectrum should also be output from the lateral suppression network 154. Further, the lateral suppression network must account for the frequency bands representing the highest and lowest frequencies of the audio signal 102, the edge frequency bands. In the system 300, for example, the first frequency band and the $k_{th}$ frequency band are the edge frequency bands. Because only one frequency band is immediately adjacent to each edge frequency band, each edge frequency band would be subjected to less suppression without additional compensation. Therefore, the lateral suppression network 154 must compensate by adjusting one or more factors, such as the weighting factor u associated with the edge frequency band or one or more of the scaling factors w employed by the lateral suppression processor associated with the edge frequency band.

The suppressed signals output from the lateral suppression network 154 are converted to electrical signals using the acoustic-to-electrical mapping associated with the corresponding frequency bands and provided as stimulation signals to one or more electrode pairs of a cochlear implant. For example, the envelope signals $E_1$ 124, $E_2$ 134, and $E_k$ 144 output from the bank of envelope detectors 116 are input into the lateral suppression network 154. The lateral suppression network 154 then suppresses one or more of the envelope signals $E_1$ 124, $E_2$ 134, and $E_k$ 144 in accordance with envelope signals associated with neighboring frequency bands, including the envelope signals $E_1$ 124, $E_2$ 134, and $E_k$ 144. The lateral suppression network 154 then outputs the corresponding suppressed signals $S_1$ 130, $S_2$ 140, and $S_k$ 150 respectively.

The suppressed signal $S_1$ 130 associated with the first frequency band is then converted into an electrical signal using the acoustic-to-electrical mapping 132 corresponding to the first frequency band. Similarly, the suppressed signal $S_2$ 140 associated with the second frequency band is then converted into an electrical signal using the acoustic-to-electrical mapping 142 corresponding to the second frequency band. Additionally, the suppressed signal $S_k$ 150 associated with the $k_{th}$ frequency band is then converted into an electrical signal using the acoustic-to-electrical mapping 152 corresponding to the $k_{th}$ frequency band.

Figure 5:
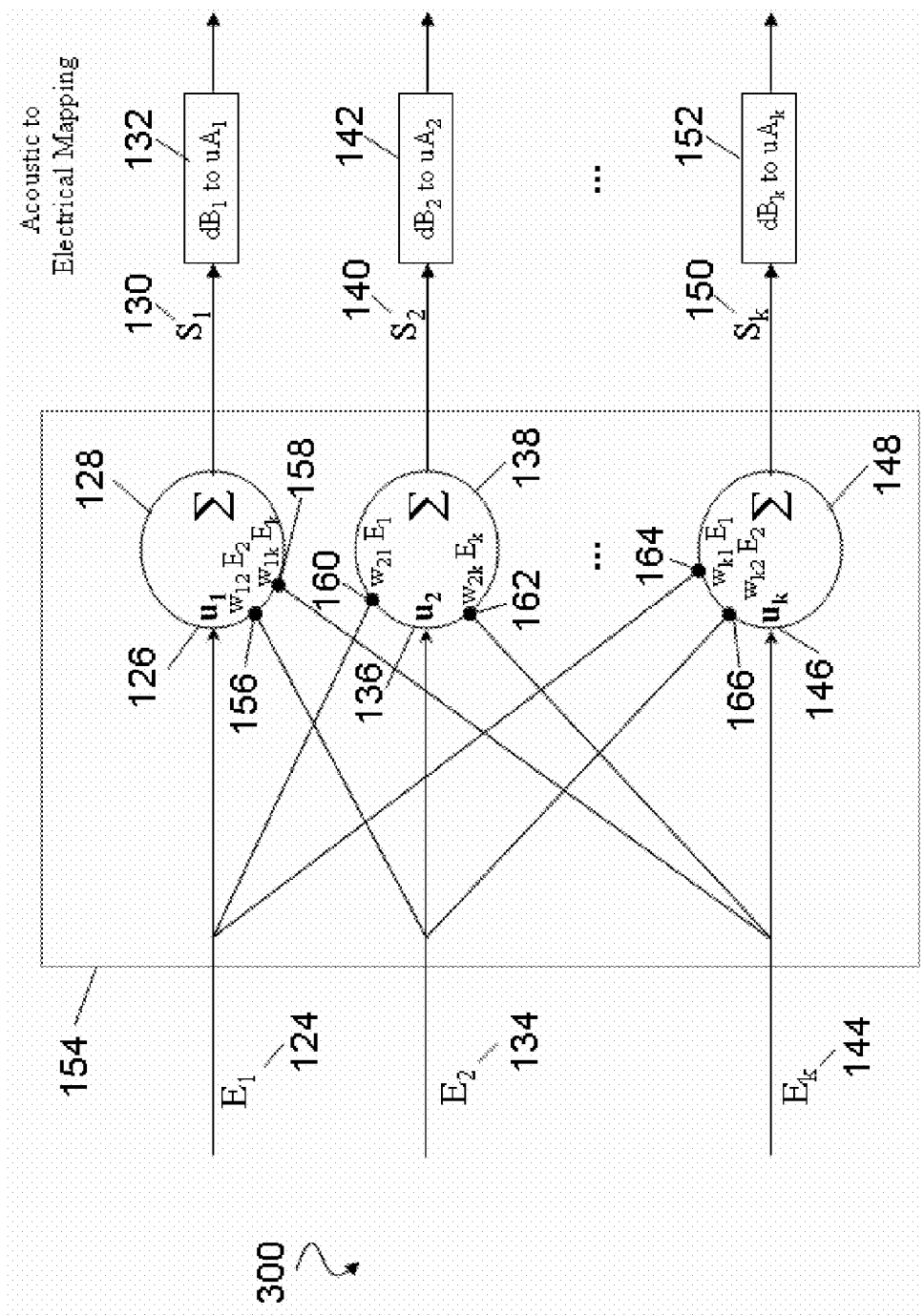
FIG. 5 is a functional block diagram of a lateral suppression network of a sound processing system.

FIG. 5 presents a functional block diagram detailing an implementation of a lateral suppression network 154 as it relates to the system 300 of FIG. 3. As described above, the envelope signals $E_1$ 124, $E_2$ 134, and $E_k$ 144 are provided as inputs to the lateral suppression network 154. In the lateral suppression network 154, each envelope signal can be combined with one or more scaled envelope signals to account for the influence that envelope signals associated with neighboring frequency bands have on a particular envelope signal.

One or more of the envelope signals output from the bank of envelope detectors 116 can be weighted by a factor $u_i$ upon being provided to the lateral suppression network 154, where i represents the frequency band with which the envelope signal is associated. Thus, an envelope signal that is determined to be of greater importance than the envelope signals associated with neighboring frequency bands can be emphasized, such as an envelope signal representing an amplitude that exceeds a particular threshold value. Further, an envelope signal determined to be of lesser importance can be deemphasized, such as an envelope signal representing an amplitude that falls below a particular threshold value. In an implementation, each of the envelope signals provided to the lateral suppression network 154 can be weighted, and the weight associated with envelope signals that should not be emphasized or deemphasized can be set to 1.

For example, the envelope signals $E_1$ 124, $E_2$ 134, and $E_k$ 144 output from the bank of envelope detectors 116 are provided as inputs to the lateral suppression network 154. The lateral suppression processor 128 corresponding to the first frequency band multiplies the envelope signal $E_1$ 124 by a weighting factor $u_1$ 126 associated with the first frequency band. Similarly, the lateral suppression processor 138 corresponding to the second frequency band multiplies the envelope signal $E_2$ 134 by a weighting factor $u_2$ 136 associated with the second frequency band. The lateral suppression processor 148 corresponding to the $k_{th}$ frequency band multiplies the envelope signal $E_k$ 144 by a weighting factor $u_k$ 146 associated with the $k_{th}$ frequency band. As a result, the suppressive effect of signals associated with neighboring frequency bands will be diminished on envelope signals deemed to be of greater importance and increased on envelope signals deemed to be of lesser importance.

Because the influence that an envelope signal has on a neighboring envelope signal decreases as the number of frequency bands separating the envelope signals increases, the scaling factor applied to an envelope signal to generate a scaled envelope signal is selected as a function of the separation of between the neighboring frequency bands. Therefore, a scaling factor $w_{ij}$ is chosen, where i represents the frequency band associated with the envelope signal being suppressed and j represents the frequency band associated with the envelope signal that is producing the suppressive effect. With each increase in the frequency band separation, the scaling factor $w_{ij}$ will further decrease the magnitude of the envelope signal being scaled. Additionally, as scaled envelope signals suppress an envelope signal, the scaling factor represents a negative value.

A laterally suppressed signal $S_i$ is generated by combining an envelope signal associated with a particular frequency band $E_i$ with one or more scaled envelope signals $w_{ij}E_j$ associated with neighboring frequency bands. As discussed above, the envelope signal being suppressed also can be weighted using a weighting factor $u_i$. The combining operation can be expressed mathematically as shown in Equation 1.

$$S_i = u_i E_i + \sum_{j \neq i} w_{ij} E_j \qquad (1)$$

Because nonlinearities are known to exist in the response of the basilar membrane, Equation 1 can be generalized as expressed in Equation 2, where $F_i(x)=X$ and $w_{ii}=0$. However, this simplification is not required and $S_i$ can be generated using a non-linear function in another implementation.

$$S_i = u_i E_i + F_i\left(\sum_j w_{ij} E_j\right) \qquad (2)$$

In an implementation, the envelope signal $E_1$ 124 associated with the first frequency band is provided to a corresponding lateral suppression processor 128. The lateral suppression processor 128 then multiplies the envelope signal $E_1$ 124 by the weighting factor $u_1$ 126. The lateral suppression processor 128 also receives as input the scaled envelope signal $w_{12}E_2$ 156, which represents the interaction of the envelope signal $E_2$ 134 associated with the second frequency band with the envelope signal $E_1$ 124 associated with the first frequency band. Additionally, the lateral suppression processor 128 receives as input the scaled envelope signal $w_{1k}E_k$ 158, which represents the interaction of the envelope signal $E_k$ 144 associated with the $k_{th}$ frequency band with the envelope signal $E_1$ 124 associated with the first frequency band. Further, the lateral suppression processor 128 can also receive as inputs the scaled envelope signals associated with any or all of the remaining third through $K-1_{th}$ frequency bands.

The lateral suppression processor 128 combines the envelope signal $E_1$ 124, weighted by $u_1$ 126, with at least the scaled envelope signals $w_{12}E_2$ 156 and $w_{1k}E_k$ 158, and outputs a laterally suppressed signal $S_1$ 130 associated with the first frequency band. The laterally suppressed signal $S_1$ 130 can then be converted to an electrical stimulation signal using the acoustic-to-electrical mapping 132 corresponding to the first frequency band.

A similar lateral suppression operation can be carried out for any or all of the envelope signals associated with the remaining frequency bands. For example, the lateral suppression processor 138 receives the envelope signal $E_2$ 134 associated with the second frequency band. The lateral suppression processor 138 then multiplies the envelope signal $E_2$ 134 by the weighting factor $u_2$ 136. The lateral suppression processor 138 also receives as inputs the scaled envelope signals $w_{21}E_1$ 160 and $w_{2k}E_k$ 162, which are associated with the first and $k_{th}$ frequency bands respectively. Additionally, the lateral suppression processor 138 can receive as inputs the scaled envelope signals associated with any or all of the remaining frequency bands. The lateral suppression processor 138 combines the envelope signal $E_2$ 134, weighted by $u_2$ 136, with the scaled envelope signals $w_{21}E_1$ 160 and $w_{2k}E_k$ 162, and outputs a laterally suppressed signal $S_2$ 140 associated with the second frequency band. The laterally suppressed signal $S_2$ 140 is then converted to an electrical stimulation signal using the acoustic-to-electrical mapping 142 associated with the second frequency band.

In an implementation, each lateral suppression processor of the lateral suppression network 154 can be configured to receive as inputs the scaled envelope signals associated with each of the neighboring frequency bands. Therefore, each of the envelope signals can be suppressed by scaled envelope signals associated with each of the neighboring frequency bands. If an envelope signal $E_b$ should not be used to suppress an envelope signal $E_a$, the scaling factor $w_{ab}$ can be set to 0.

Figure 6:
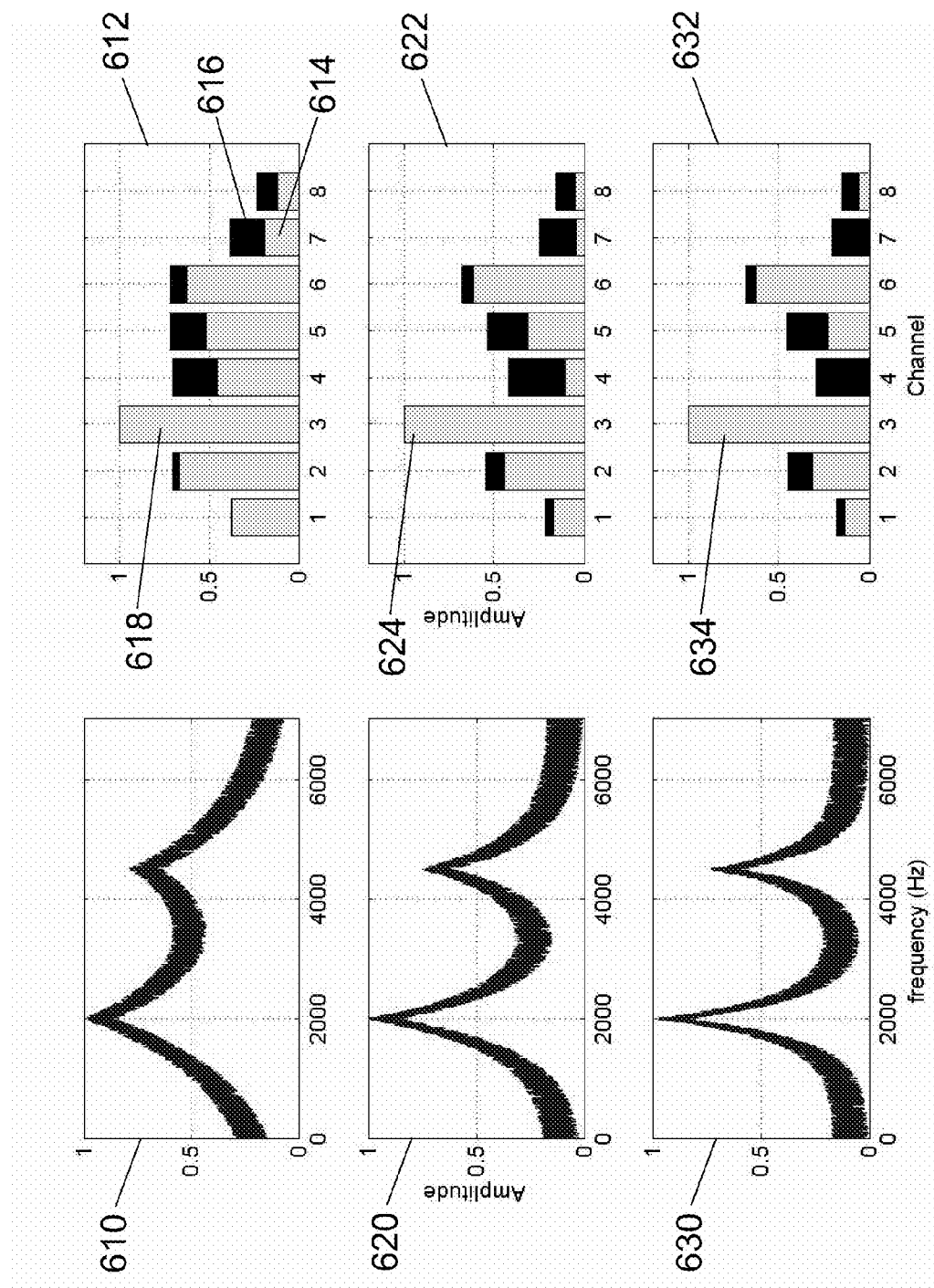
FIG. 6 presents results comparing a Continuous Interleaved Sampler (CIS) strategy used in conjunction with an outer hair cell model and a CIS strategy used without an outer hair cell model.

FIG. 6 presents a graphical comparison of the stimulation signals generated in response to varying input signals using the CIS strategy employed in conjunction with the outer hair cell model and the CIS strategy employed without the outer hair cell model. The spectrum of the stimulation signals generated in response to the first input signal 610 using CIS processing in conjunction with the outer hair cell model are indicated in the first bar graph 612 by light colored bars, such as the light bar 614 associated with channel 7. The spectrum of the stimulation signals generated in response to the first input signal 610 using CIS processing without the outer hair cell model are indicated in the first bar graph 612 using dark colored bars, such as the dark bar 616 associated with channel 7.

As the amplitude of the dark colored bars always equals or exceeds the amplitude of the light colored bars, the dark colored bars are depicted behind the light colored bars. Each of the dark colored bars and each of the light colored bars represents an amplitude of a stimulation signal corresponding to a particular channel. Where a dark colored bar is visible, such as the dark colored bar 616 associated with channel 7, the amplitude of the stimulation signal generated using CIS processing without the outer hair cell model exceeds the amplitude of the stimulation signal generated using CIS processing in conjunction with the outer hair cell model.

As depicted in the first bar graph 612, even though the spectrum of the first input signal 610 is relatively flat, CIS processing used in conjunction with the outer hair cell model produces stimulation signals characterized by greater channel-to-channel amplitude differences than the stimulation signals produced using CIS processing without the outer hair cell model. This is especially true for channels adjacent to signal peaks, such as the stimulation signal represented by the light bar 618 of channel 3. Therefore, CIS processing performed in conjunction with the outer hair cell model provides enhanced stimulation signal contrast over CIS processing performed without the outer hair cell model.

The second bar graph 622 corresponding to the second input signal 620 indicates that as the peaks in the spectrum of the input signal become more pronounced, CIS processing in conjunction with the outer hair cell model produces stimulation signals characterized by even greater channel-to-channel amplitude differences than the stimulation signals produced using CIS processing without the outer hair cell model. As discussed above, this is especially true for channels adjacent to peaks in the spectrum, such as the stimulation signal represented by the light bar 624 of channel 3.

The third bar graph 632 corresponding to the third input signal 630 provides further indication that, as the peaks of the spectrum of the input signal become very pronounced, CIS processing in conjunction with the outer hair cell model produces stimulation signals characterized by even greater channel-to-channel amplitude differences than the stimulation signals produced using CIS processing without the outer hair cell model. Again, this is especially true for channels adjacent to large peaks in the spectrum, such as the stimulation signal 634 of channel 3.

Figure 7:
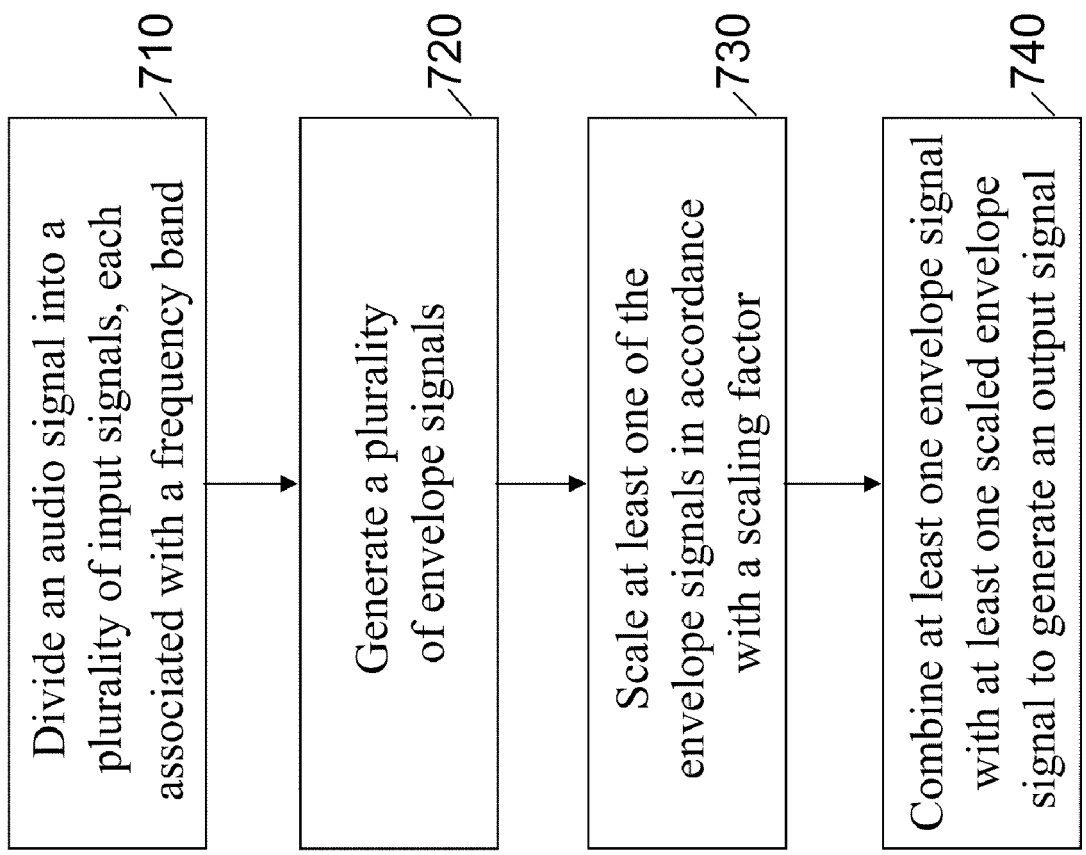
FIG. 7 is a flowchart of a method of stimulating a cochlea.

FIG. 7 describes a method of stimulating a cochlea using a lateral suppression strategy, such as the outer hair cell model. In a first step 710, as described above, an audio signal 102 is divided into a plurality of input signals using a bank of band-pass filters 104. Each of the input signals generated from the audio signal 102 is associated with a frequency band. In a second step 720, a plurality of envelope signals, including at least a first and second envelope signal, are generated by a bank of envelope detectors 106. The individual envelope detectors included in the bank of envelope detectors 106 each determine an envelope of an input signal associated with a corresponding frequency band. Once the plurality of envelope signals has been generated, the third step 730 is to scale at least one envelope signal in accordance with a scaling factor to generate a scaled envelope signal. This step generates signals for use in the lateral suppression network 154. In a fourth step 740, at least one envelope signal is combined with at least one scaled envelope signal to generate an output signal.

A number of implementations have been disclosed herein. Nevertheless, it will be understood that various modifications may be made without departing from the spirit and scope of the claims. Accordingly, other implementations are within the scope of the following claims.

What is claimed is:

1. A method of generating cochlear stimulation signals for use in a cochlear implant, the method comprising:
    filtering an audio signal into a plurality of input signals, wherein each input signal comprises a band of frequencies from the audio signal;
    determining an envelope signal for each of the input signals, wherein each envelope signal is indicative of the magnitude of its corresponding input signal;
    determining a suppression signal for each of the envelope signals, wherein each suppression signal is determined as a function of its corresponding envelope signal and at least one other non-corresponding envelope signal; and
    producing a plurality of cochlear stimulation signals each corresponding to a particular electrode of the cochlear implant, wherein each cochlear stimulation signal is produced from one of the plurality of suppression signals.

2. The method of claim 1, wherein each suppression signal comprises a weighted sum of its corresponding envelope signal and at least one other non-corresponding envelope signal.

3. The method of claim 1, wherein each suppression signal comprises a weighted sum of its corresponding envelope signal and an adjacent other non-corresponding envelope signal.

4. The method of claim 1, wherein a corresponding envelope signal comprises $E_i$, at least one other non-corresponding envelope signal comprises $E_j$, and wherein the determined suppression signal $S_i$ comprises:

$$S_i = u_i E_i + F_i\left(\sum_j w_{ij} E_j\right)$$

wherein $u_i$ comprises a weighting factor and $w_{ij}$ comprises a scaling factor.

5. The method of claim 1, wherein each of the bands of frequencies are mapped to electrodes on the cochlear implant by a sound processing strategy.

6. The method of claim 5, wherein the sound processing strategy comprises one of a simultaneous analog stimulation strategy, a continuous interleaved sampler strategy, and a frequency modulated stimulation strategy.

7. The method of claim 1,
wherein a first contrast exists between adjacent envelope signals; and
wherein determining the suppression signals comprises modifying each envelope signal to form each suppression signal, wherein the suppression signals comprise a second contrast between adjacent suppression signals different from the first contrast.

8. The method of claim 7, wherein at least one of the envelope signals represents a spectral peak, and wherein modifying each envelope signal to form a corresponding suppression signal comprise decreasing at least one suppression signals adjacent to the peak.

9. The method of claim 7, wherein the second contrast is larger than the first contrast.

* * * * *